United States Patent
Tatsumi

(10) Patent No.: US 9,770,342 B2
(45) Date of Patent: Sep. 26, 2017

(54) INTERSPINOUS SPACER AND FACET JOINT FIXATION DEVICE

(71) Applicant: WARSAW ORTHOPEDIC, INC., Warsaw, IN (US)

(72) Inventor: Robert L. Tatsumi, Lake Oswego, OR (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/584,093

(22) Filed: Dec. 29, 2014

(65) Prior Publication Data

US 2015/0112441 A1 Apr. 23, 2015

Related U.S. Application Data

(63) Continuation of application No. 13/147,588, filed as application No. PCT/US2010/000291 on Feb. 2, 2010, now Pat. No. 8,920,504.

(60) Provisional application No. 61/403,727, filed on Apr. 13, 2009.

(51) Int. Cl.
*A61F 2/44* (2006.01)
*A61B 17/17* (2006.01)
*A61B 17/70* (2006.01)

(52) U.S. Cl.
CPC ........ *A61F 2/4455* (2013.01); *A61B 17/1757* (2013.01); *A61B 17/7064* (2013.01); *A61F 2/442* (2013.01); *A61B 17/7071* (2013.01)

(58) Field of Classification Search
CPC .......................... A61F 2/4455; A61B 17/1757
USPC .............. 606/60, 246–279; 623/17.11–17.16
See application file for complete search history.

(56) References Cited

U.S. PATENT DOCUMENTS

| | | |
|---|---|---|
| 5,527,312 A | 6/1996 | Ray |
| 5,766,252 A | 6/1998 | Henry et al. |
| 6,419,703 B1 | 7/2002 | Fallin et al. |
| 6,540,747 B1 | 4/2003 | Marino |
| 6,743,255 B2 | 6/2004 | Ferree |
| 6,902,580 B2 | 6/2005 | Fallin et al. |
| 6,979,353 B2 | 12/2005 | Bresina |
| 7,074,237 B2 | 7/2006 | Goble et al. |
| 7,090,698 B2 | 8/2006 | Goble et al. |
| 7,306,628 B2 | 12/2007 | Zucherman et al. |
| 7,377,942 B2 | 5/2008 | Berry |
| 7,566,345 B1 | 7/2009 | Fallin et al. |

(Continued)

FOREIGN PATENT DOCUMENTS

| | | |
|---|---|---|
| EP | 1132053 A1 | 9/2001 |
| JP | 975381 A | 3/1997 |

(Continued)

OTHER PUBLICATIONS

LANX, Telluride MIS Spinal Fixation System, product advertisement, printed 2008, pp. 1-2.

(Continued)

*Primary Examiner* — Christopher Beccia

(57) ABSTRACT

A biologically implantable device including a spacer body and fasteners for fixing the spacer body in place between vertebrae, and a method for use of the device to improve intervertebral spacing and correct foraminal stenosis, and to immobilize facet joints and promote fusion of adjacent vertebrae to each other. A drill guide may be used in providing bores in the facet joints to receive the fasteners.

15 Claims, 7 Drawing Sheets

(56) References Cited

U.S. PATENT DOCUMENTS

| | | | |
|---|---|---|---|
| 7,621,951 B2 | 11/2009 | Glenn et al. | |
| 7,763,078 B2 * | 7/2010 | Peterman | A61F 2/4455 606/246 |
| 7,985,244 B2 * | 7/2011 | Borgstrom | A61B 17/7023 606/249 |
| 8,920,504 B2 | 12/2014 | Tatsumi | |
| 2003/0040746 A1 | 2/2003 | Mitchell et al. | |
| 2004/0254575 A1 | 12/2004 | Obenchain et al. | |
| 2005/0027361 A1 | 2/2005 | Reiley | |
| 2005/0055096 A1 | 3/2005 | Serhan et al. | |
| 2005/0149030 A1 | 7/2005 | Serhan et al. | |
| 2006/0106381 A1 | 5/2006 | Ferree et al. | |
| 2006/0235391 A1 | 10/2006 | Sutterlin, III | |
| 2006/0241601 A1 | 10/2006 | Trautwein et al. | |
| 2006/0241610 A1 * | 10/2006 | Lim | A61B 17/7067 606/249 |
| 2006/0241757 A1 * | 10/2006 | Anderson | A61B 17/7062 623/17.11 |
| 2006/0247632 A1 * | 11/2006 | Winslow | A61B 17/025 606/247 |
| 2006/0276790 A1 | 12/2006 | Dawson et al. | |
| 2007/0088358 A1 | 4/2007 | Yuan et al. | |
| 2007/0191834 A1 * | 8/2007 | Bruneau | A61B 17/7067 606/279 |
| 2007/0233083 A1 | 10/2007 | Abdou | |
| 2007/0270840 A1 | 11/2007 | Chin et al. | |
| 2008/0027438 A1 | 1/2008 | Abdou | |
| 2008/0082172 A1 | 4/2008 | Jackson | |
| 2008/0097446 A1 | 4/2008 | Reiley et al. | |
| 2008/0140125 A1 | 6/2008 | Mitchell et al. | |
| 2008/0177306 A1 | 7/2008 | Lamborne et al. | |
| 2008/0183211 A1 | 7/2008 | Lamborne et al. | |
| 2008/0234735 A1 | 9/2008 | Joshi | |
| 2008/0281360 A1 | 11/2008 | Vittur et al. | |
| 2008/0281361 A1 | 11/2008 | Vittur et al. | |
| 2009/0264927 A1 | 10/2009 | Ginsberg et al. | |
| 2010/0023059 A1 | 1/2010 | Dewey et al. | |

FOREIGN PATENT DOCUMENTS

| | | |
|---|---|---|
| JP | 200379649 A | 3/2003 |
| WO | 2006110767 A1 | 10/2006 |
| WO | 2010120333 A1 | 10/2010 |

OTHER PUBLICATIONS

LANX, Aspen Spinous Process Fixation System, product advertisement, printed 2009, pp. 1-2.

Synthes, The Vectra System anterior cervical plating system, website product advertisement/description, retrieved from the Internet on Jan. 27, 2010, 1 pg.

Stryker Corporation, Stryker Reflex Hybrid ACP Implant, website product advertisement/description, retrieved from the Internet Jan. 12, 2012, 1 pg.

Globus Medical, Coalition Integrated Plate and Spacer ACDF System, product advertisement, 1 pg.

\* cited by examiner

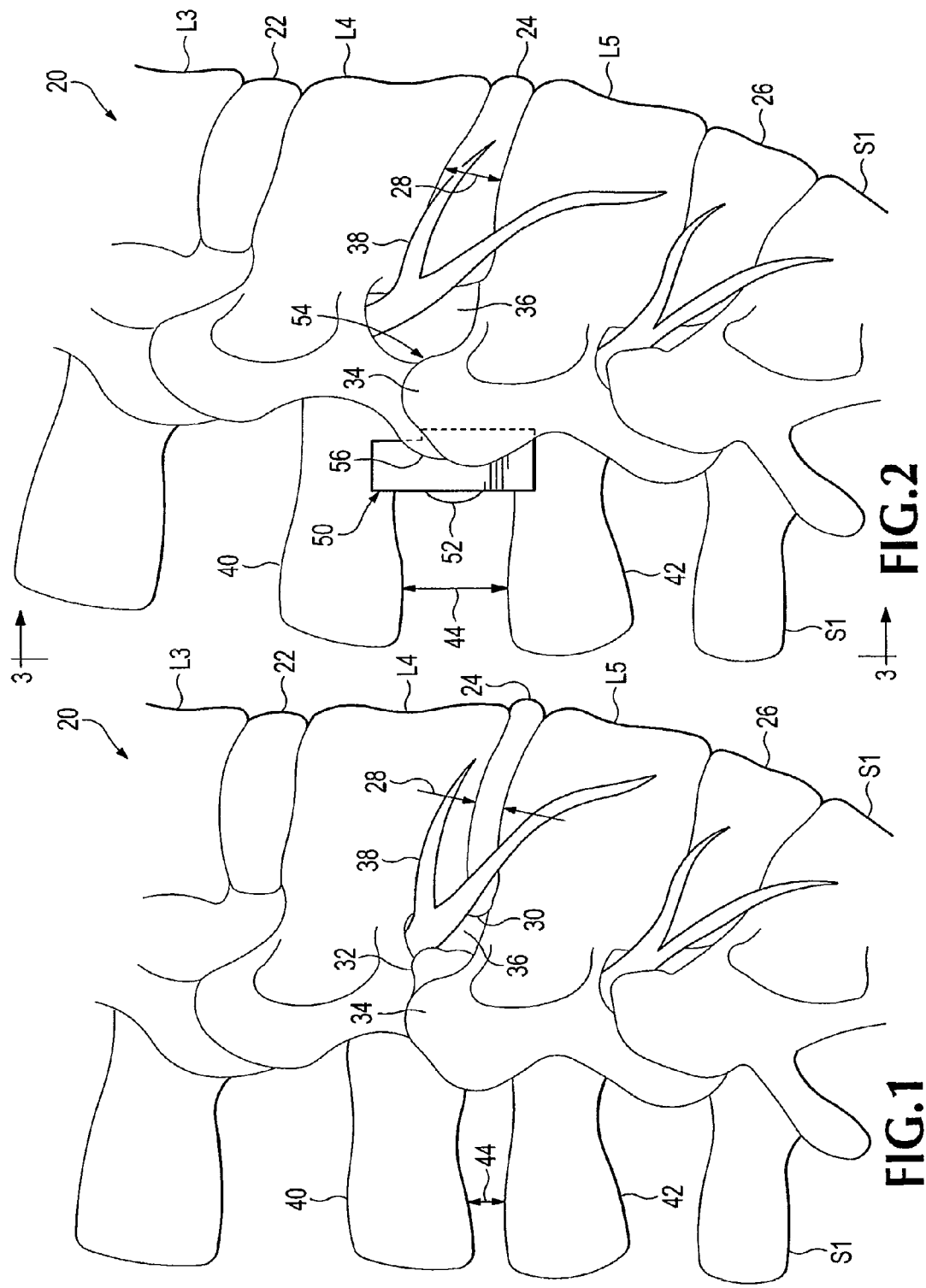

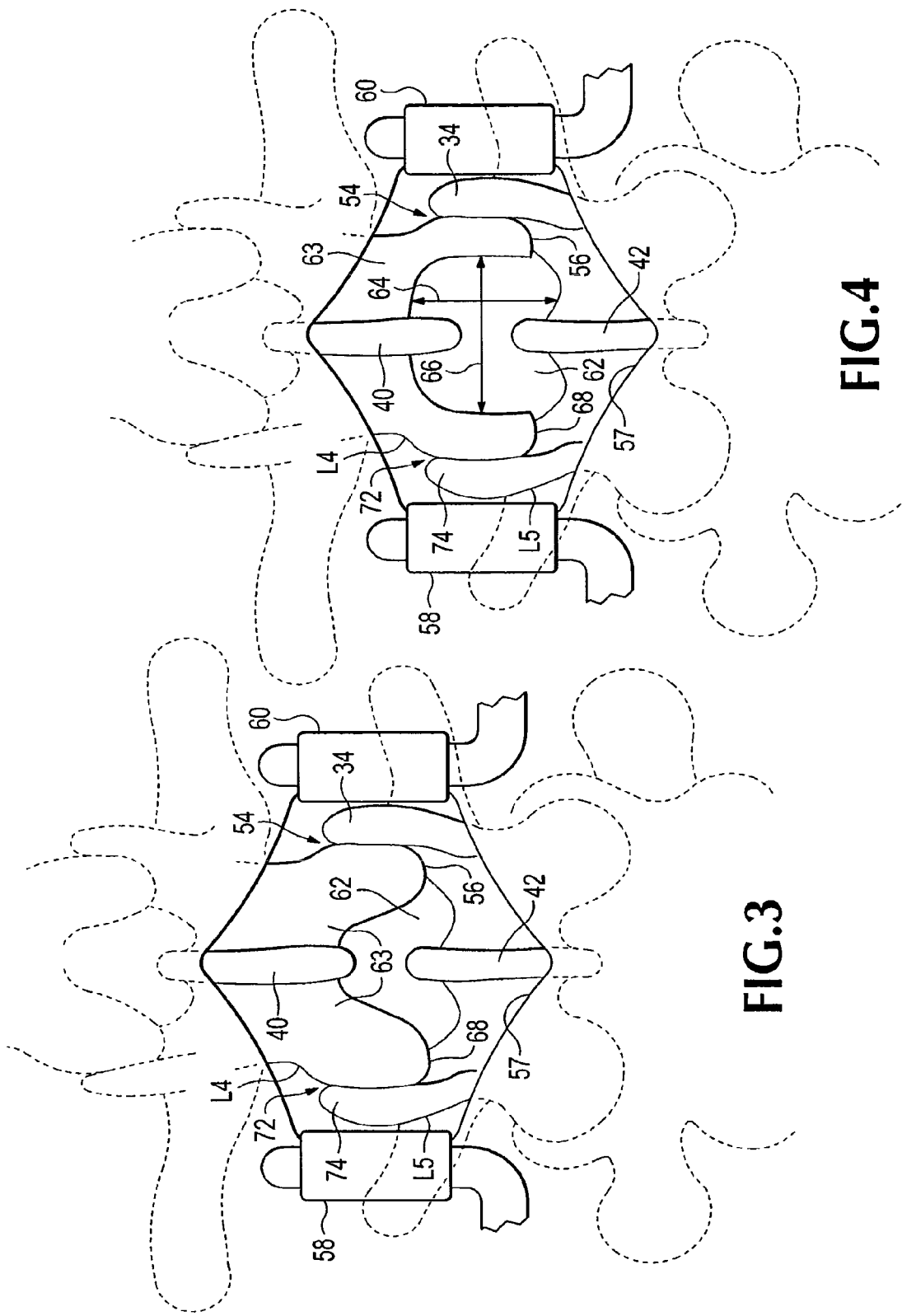

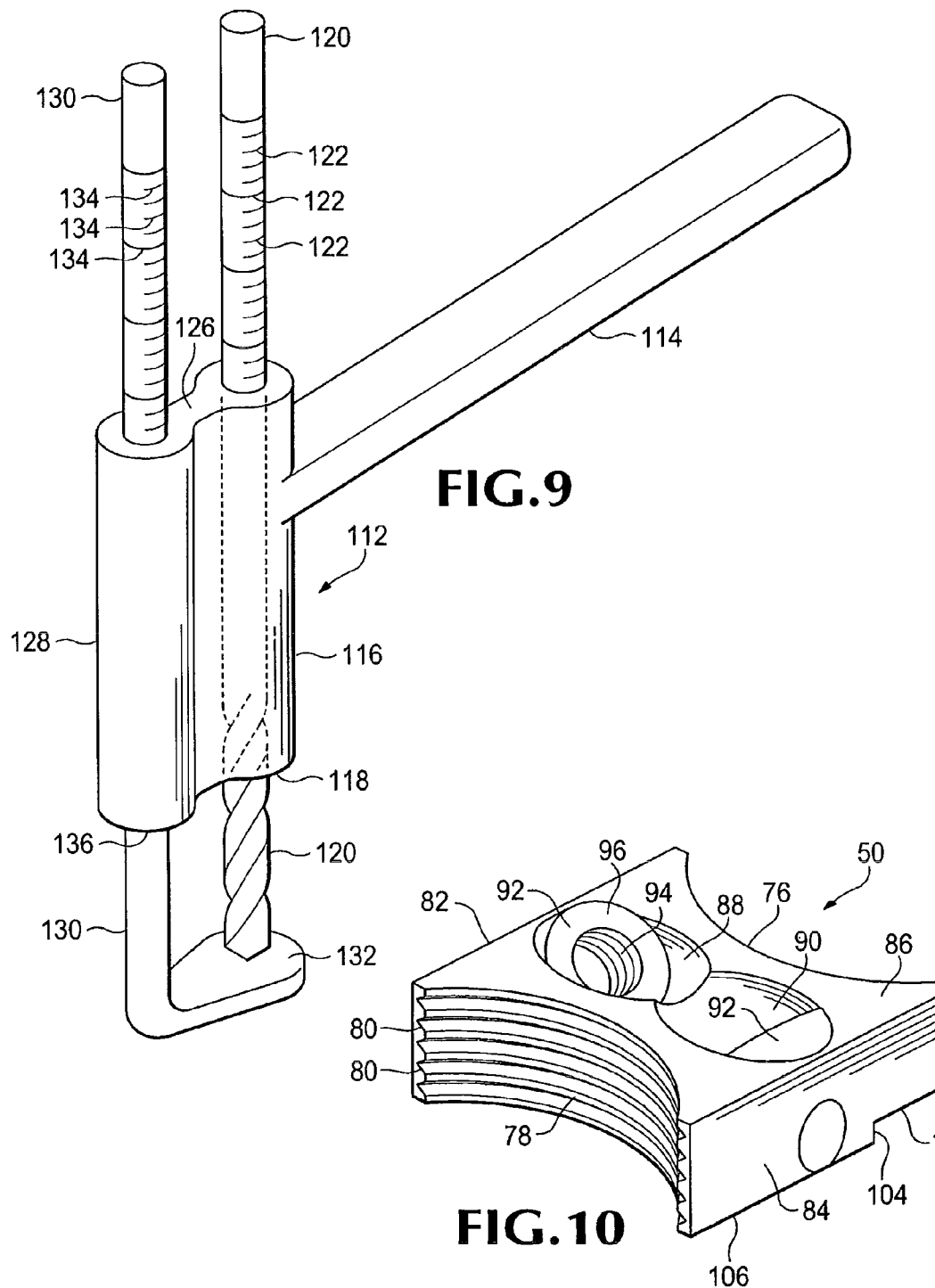

INTERSPINOUS SPACER AND FACET JOINT FIXATION DEVICE

TECHNICAL FIELD

The present invention relates to spinal surgery, and in particular relates to an implantable device and a procedure for use of such a device in fusing vertebrae together.

BACKGROUND ART

Lower back pain is commonly caused by deterioration of intervertebral discs and facet joints, resulting in stenosis of intervertebral foramina and thus causing pressure on spinal nerve roots where they exit from the spinal nerve canal and extend laterally away from the spine through the intervertebral foramina. As people age, intervertebral discs and other parts of the spinal column deteriorate. Discs may shrink, allowing vertebrae to approach one another more closely, and facet joints may develop bone spurs, protruding into the foramina and reducing the available space through which nerve roots must extend. Pressure on nerve roots due to facet arthrosis, ligamentum flavum infolding, and disc herniations often results and can cause severe and even debilitating pain. Degeneration of discs may also allow a vertebra to become misaligned with respect to an adjacent vertebra, resulting in spondylolisthesis.

It is well known to decompress the spine, that is, to relieve pressure on the spinal exiting and traversing nerves by performing bilateral laminotomies and to immobilize adjacent vertebrae with respect to each other. Installing pedicle screws and rods can also be used to stabilize the spine if necessary.

It is also known that facet joints can be immobilized, and that a lumbar vertebra can be fused together with an adjacent lumbar vertebra to prevent the vertebrae from moving relative to each other, in order to prevent future impingement on spinal nerves between the fused vertebrae. In the past, however, vertebral fusion has typically been accomplished by the use of pedicle screws and rods to immobilize vertebrae relative to each other. Compared with facet fixation, pedicle screws and rod insertions requires a longer operative time, and results in increased blood loss, and increased paraspinal muscle trauma. Since spinal deterioration of the sort which requires such surgical remedy usually occurs in older patients, it would be desirable to be able to immobilize and fuse vertebrae in a procedure that takes less time, less anesthesia, less blood loss, and less soft tissue trauma.

Recently, less invasive procedures have been utilized, such as percutaneous installation of screws into facet joints to immobilize them, as disclosed, for example, in Serhan et al. U.S. Patent Application Publication Document No. US2005/0149030-A1. It is also known to insert a long screw through a spinous process and into a facet joint, as shown in Obenchain et al. U.S. Patent Application Publication Document No. US2004/0254575-A1.

Many different methods and devices are known for use in immobilizing vertebrae relative to one another to promote fusion. One type of device intended for immobilizing adjacent lumbar vertebrae with respect to each other includes a spinous process fixation system in which a clamp is fastened to the spinous processes of two adjacent vertebrae, fastening them together. Such devices are disclosed in Chin et al. U.S. Patent Application Publication Document No. US2007/0270840-A1 and Lamborne et al. U.S. Patent Application Publication Document No. US2008/0183211-A1. Such clamps can be attached so as to distract the vertebrae from each other, but because of the location of such a clamp, spaced apart dorsally from the deteriorated intervertebral discs, use of such a clamp may result in reduced lordosis, thereby resulting in additional strain experienced by joints between other vertebrae. Such clamp devices, moreover, often cannot be used in an L5-S1 location, because of the lack of a large enough spinous process on the sacrum. Additionally, the interconnected spinous processes may fail under the forces applied through such clamps.

What is desired, then, is a device and a method for its use in relieving pressure on spinal nerves and in fusing vertebrae together, using a minimally invasive procedure that can be performed in a significantly shorter time than has previously been required for vertebral fusion procedures such as those including the installation of pedicle screws and rods.

DISCLOSURE OF INVENTION

The present invention provides answers to some of the above-described needs and shortcomings of previously known devices and procedures, as defined by the claims appended hereto.

According to a principal aspect of the present invention, an implantable device includes a spacer body that can be implanted between the spinous processes and between the articulating processes of a pair of adjacent vertebrae that are to be fused together. The spacer body supports the vertebrae in a desired relationship. A pair of fasteners such as screws extend through the spacer body, with each screw extending also through the facet joint on a respective lateral side of the spine so as to immobilize the facet joint and promote fusion between the cephalad/caudad lamina, spinous process, and facet joints.

As an aspect of one embodiment of the implantable device disclosed herein, locking devices are provided in the spacer body to ensure that fasteners installed to hold the spacer device in place and to immobilize facet joints are kept in place relative to the spacer body.

Another aspect of the device and procedure disclosed herein is that a drill guide may be used in conjunction with the spacer body to direct a drill or similar tool used to prepare a hole in the facet joint and aligned with a fastener receptacle in the spacer body to receive a fastener to immobilize the facet joint on each lateral side of the location of the spacer body.

The foregoing and other features of the invention will be more readily understood upon consideration of the following detailed description of the invention taken in conjunction with the accompanying drawings.

BRIEF DESCRIPTION OF THE DRAWINGS

FIG. 1 is a side elevational view of a lower portion of a human spine in which an intervertebral disc has deteriorated.

FIG. 2 is a view similar to FIG. 1, showing the same portion of a spine after performance of a surgical procedure as disclosed herein to fuse two vertebrae together.

FIG. 3 is a view taken in the direction indicated by the line 3-3 in FIG. 2, showing a portion of the spine shown in FIG. 2 surgically exposed for performance of corrective surgery in accordance with the present invention.

FIG. 4 is a view similar to FIG. 3, showing the portion of a spine after completion of a bilateral laminotomy on the cranial one of the exposed vertebrae.

FIG. 9 is an isometric view of a drill guide for use in connection with implantation of the fusion-promoting spacer body.

FIG. 10 is an isometric view of the interspinous process spacer body portion of the fusion-promoting device, at an enlarged scale.

DETAILED DESCRIPTION OF MODES FOR CARRYING OUT THE INVENTION

Figure 5:
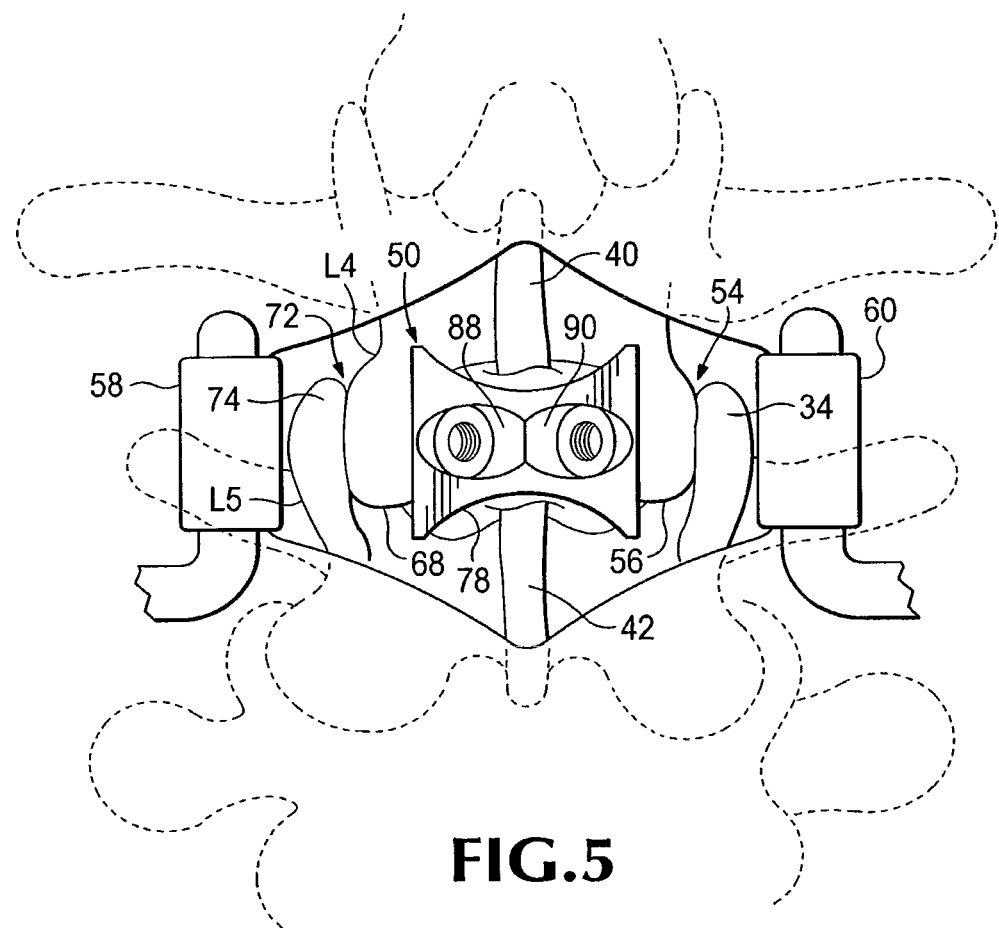
FIG. 5 is a view similar to FIG. 4, showing a vertebral fusion-promoting spacer body in place between the spinous processes, which are shown partially cut away for clarity.

Referring now to the drawings, which form a part of the disclosure herein, in FIG. 1 a part of a spinal column 20 is seen in profile from the right lateral side. The illustrated part of the spinal column includes a sacrum S1 and lumbar vertebrae L5, L4, and L3. Intervertebral discs 22, 24, and 26 separate the vertebrae from one another and, in a healthy individual, maintain sufficient spacing between adjacent vertebrae.

In the spinal column 20 as shown in FIG. 1, however, the disc 24 between the L4 and L5 vertebrae has deteriorated and has allowed the spacing 28 between the L4 and L5 vertebrae to decrease markedly from normal spacing. The L4 vertebra has also been able to move ventrally with respect to the L5 vertebra, and the disc 24 is herniated and has bulged in a dorsal direction, as shown at 30. The superior articulating process 34 of the L5 vertebra has become hypertrophied, and an osteophyte, or bone spur 32 protrudes from it toward the nerve root 38.

The combination of these defects or abnormalities in the L4-L5 location causes a stenosis, or reduction of the size, of the foramen 36, that can result in pressure on the spinal nerve 38 where it exits from the spinal column between the L4 and L5 vertebrae. The spinous process 40 of the L4 vertebra is shown in FIG. 1 to have approached the spinous process 42 of the L5 vertebra, so that the vertical distance 44 between the spinous processes 40 and 42 has been significantly reduced from normal.

As shown in FIG. 2 the spinal column 20 has been surgically repaired. The L4 and L5 vertebrae have been moved apart from one another and are held in a more desirable relationship to each other by the implantation of an interspinous process spacer body 50 located between the spinous processes 40 and 42 to increase the vertical distance 44. Screws 52 are mounted in the spacer body 50 and extend into the right facet joint 54 and the left facet joint (not seen), fastening together and immobilizing the superior articulating process 34 of the L5 vertebra and the inferior articulating process 56 of the L4 vertebra, and the corresponding parts of the left facet joint.

As shown in FIGS. 3-6, the spacer body 50 and a pair of fasteners such as screws 52 are implanted surgically through an incision 57 in a patient's back in the vicinity of the vertebrae (L4 and L5, as shown) that need to be fused together. The incision may be made along the midline from about the middle of the spinous process 40 of the cranial one of the affected vertebrae to about the middle of the spinous process 42 of the caudal one of the affected vertebrae. As shown in FIG. 3, the incision is made along a medial line over the spinous processes 40 and 42, after which skin, connective tissue, and muscle are retracted laterally by retractors 58 and 60.

The spinous processes 40 and 42 are exposed, the interspinous ligament is excised, and a bilateral hemilaminotomy may be performed on the cranial one of the vertebrae, if necessary, to enlarge the space 62 between the affected vertebrae, in this case the L4 and L5 vertebrae as shown in FIG. 4. Laminotomy may not be required at all, or may be required for both vertebrae involved, as may be determined by the surgeon. Although the caudally located vertebra L5 may undergo a laminotomy, in most cases laminotomy will not be required in the caudal one of a pair of vertebrae to be fused together. The ligamentum flavum is removed from the space 62 between the vertebrae and exposed surfaces of the remaining parts of the laminae 63 may be partially decorticated to enhance in-growth of bone tissue from the L4 and L5 vertebrae in order to fuse the two vertebrae together into a rigidly unified structure.

After completion of bilateral hemilaminotomy and removal of ligamentum flavum the enlarged foramen 36 is examined to ascertain that the exiting nerve root and the traversing nerve root have been decompressed and are clearly free of impingement of the remaining portions of the laminae 63 and the facet joints 54 and 72 of the vertebrae concerned.

Referring next to FIG. 5, the surgeon selects from a set of similar spacer bodies of different sizes a spacer body 50 of what appears to be an appropriate size and inserts it, between the cranially located spinous process 40 and the caudally located spinous process 42, into the space 62 defined between the remaining portions of the laminae 63 of the vertebrae L4 and L5, to determine that the selected spacer body 50 will provide the desired height 64, as shown in FIG. 4, and to ensure that the selected spacer body 50 correctly fits within the width 66 of the space between the inferior articulating processes 56 and 68 of the L4 vertebra, the cranially-located one of the pair of vertebrae to be fused together. The spacer body 50 of the correct size should fit snugly but easily into that space, maintaining the increased height 64 between vertebrae L4 and L5 to compensate for the collapsed intervertebral disc 22. When the correct size has been determined, the appropriate spacer body 50 is inserted between the spinous processes 40 and 42 and fitted into the space between the vertebrae concerned, to enlarge the vertical distance 44 and the height 64 and preserve an enlarged space 62.

Once the spacer body 50 has been installed, it is necessary to provide an opening to receive a fastener 52 to fix together and promote fusion of the superior and inferior articulating processes. While this can be done by an experienced surgeon without mechanical guidance, it is preferred to use a tool such as the drill guide 112 shown in FIGS. 7 and 9 to bore a fastener hole through the facet joint 54 or 72 in an optimal location and direction. Additionally, the use of a drill guide 112 can assist in determining the required length for a fastener 52 to be inserted through the spacer body 50 into each of the facet joints 54 and 72.

The drill guide 112 may include a handle 114 attached to a drill guide tube 116 whose distal end 118 may be shaped appropriately to fit against a selected portion of the fastener receptacle 88 or 90 of the spacer body 50. A drill 120 may be provided specifically for use with the drill guide 112 and may be marked with graduations 122 along its shank to provide a direct indication of the distance by which the drill 120 extends beyond the distal end 118, or to provide a direct indication of an appropriate length of screw 52 to be used, based upon the final position of the drill 120 when it has proceeded through both the inferior articulating process 68 of the cranial vertebra and the superior articulating process 74 of the caudal (L5) vertebra.

Spaced apart from the drill guide tube 116 by a spacer member 126 of an appropriate size is a feeler guide tube 128 in which a feeler probe 130 is slidably carried. A distal end portion 132 of the feeler 130 may be bent at an appropriate angle to fit against a lateral aspect of a superior articulating process 74, in order to assure that the guide tube 116 is oriented as required for the drill 120 to form a bore in an appropriate location passing through the articulating processes 56 and 34 or 68 and 74. Instead of, or in addition to the scale graduations 122 that may be provided on a drill 120 for use with the drill guide 112, a scale of graduation marks 134 may be provided on the shank of the feeler 130 to provide an indication of the distance between the distal end 136 of the feeler guide tube 128 and the tip portion 132 of the feeler 130, as an indication of an appropriate length for a screw 52 to be used with the spacer body 50.

Figure 7:
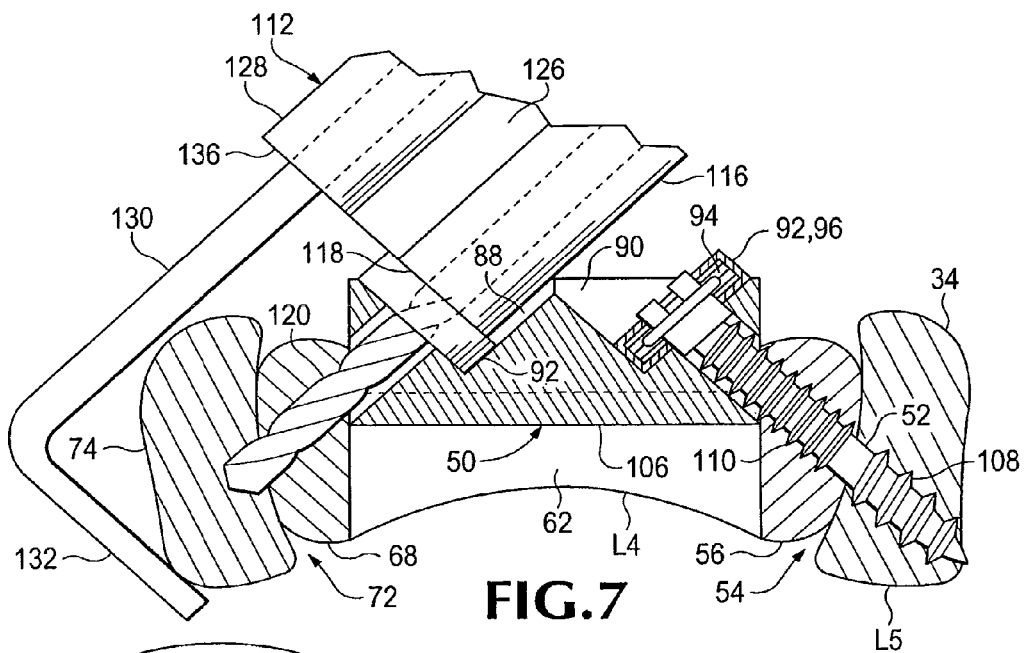
FIG. 7 is a sectional view taken on line 7-7 of FIG. 6.
Figure 16:
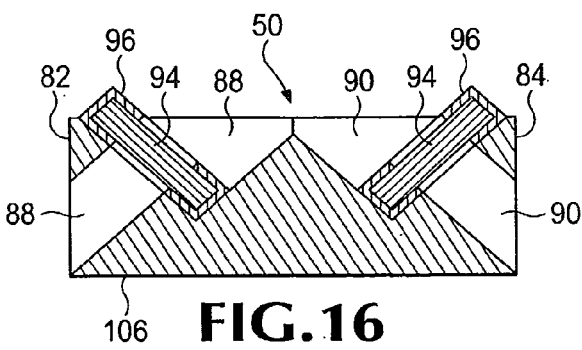
FIG. 16 is a sectional view through the spacer body, taken along line 13-13 of FIG. 9.

Once the screws 52 or other appropriate fasteners have been inserted and tightened, they may be retained and prevented from loosening with respect to the spacer body 50 by locking devices 92 that may be mounted in the fastener receptacles 88 and 90 in the spacer body 50, as shown in FIGS. 5, 7, and 16.

As may be seen in FIGS. 10-16, the intervertebral spacer body 50 may be a generally "H"-shaped or bowtie-shaped body with a pair of opposite generally concave sides, a first, bone-engagement or cranial vertebra engagement face 76 and a second bone-engagement, or caudal vertebra engagement face 78. Each of these faces may include a non-slip surface shape or texture, such as the narrow parallel grooves 80 extending along the caudal bone engaging face 78 as may be seen best in FIG. 10 and FIG. 11. Opposite lateral end faces, a left end face 82 and a mirror-opposite right end face 84, shown in FIG. 14, extend between the bone engagement faces 76 and 78. The lateral end faces 82 and 84 may conveniently be made flat, but may also be otherwise shaped, such as being convexly curved surfaces, depending on how the spacer 50 is made. A dorsal face 86 may be generally flat, as shown, but its precise shape also is not critical, and depending on how the spacer body 50 is manufactured the dorsal face 86 may instead be generally flat or convexly rounded and may have any desired surface texture or may be treated or coated with a known material to promote adhesion of new bone growth to incorporate the spacer body 50 into the vertebrae being fused together.

Extending into the dorsal face 86 at an acute angle and proceeding diagonally toward the left and right end faces 82 and 84 are a pair of fastener receptacles 88 and 90, each opening laterally outward through a respective one of the end faces 82 and 84. The fastener receptacles 88 and 90 are formed to provide a secure purchase for the fastener to secure the spacer body 50 yet permit some angular variation of the generally ventrally inclined orientation of a fastener 52 where it extends laterally outwardly from one of the lateral end faces 82 and 84.

Each fastener receptacle preferably includes a fastener locking device 92 that is fixedly attached to the spacer body 50 to keep a fastener such as a bone screw 52 fitted in the fastener receptacle 88 or 90 from loosening and backing out of the desired position once it has been installed as shown above in FIG. 6. Such a fastener locking device 92 may be of any desired functionally operable type. For example, a locking device may include a spring 94 captured within a radially inwardly open channel defined by a shell 96 as shown in FIG. 16, with the spring 94 arranged to receive and lock around a radially-extending ridge 98 on a screw 100 as shown in FIG. 7.

Figure 6:
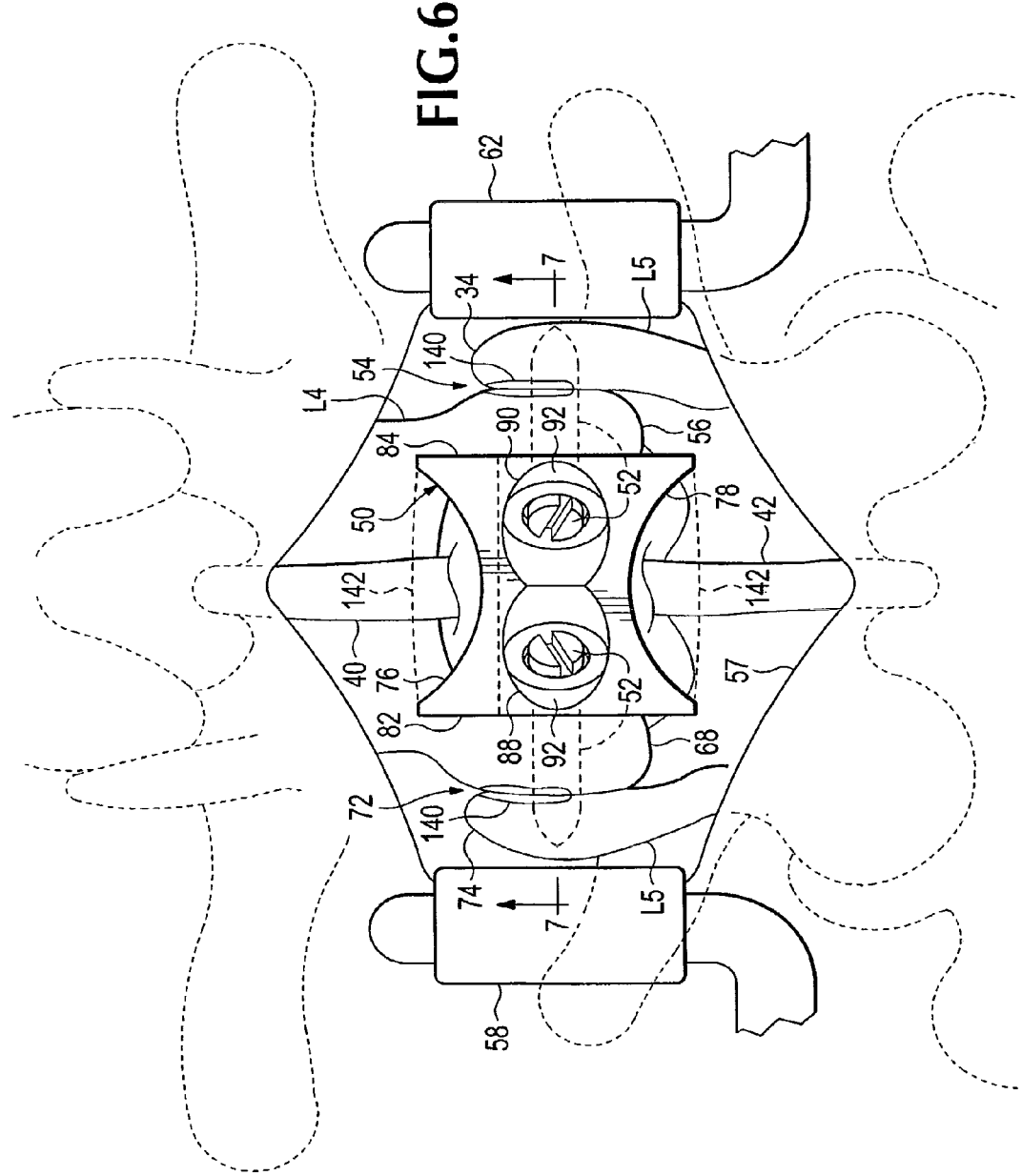
FIG. 6 is a view similar to FIG. 5, showing a vertebral fusion-promoting spacer and facet joint fixation device installed in the exposed portion of the spine.
Figure 8:
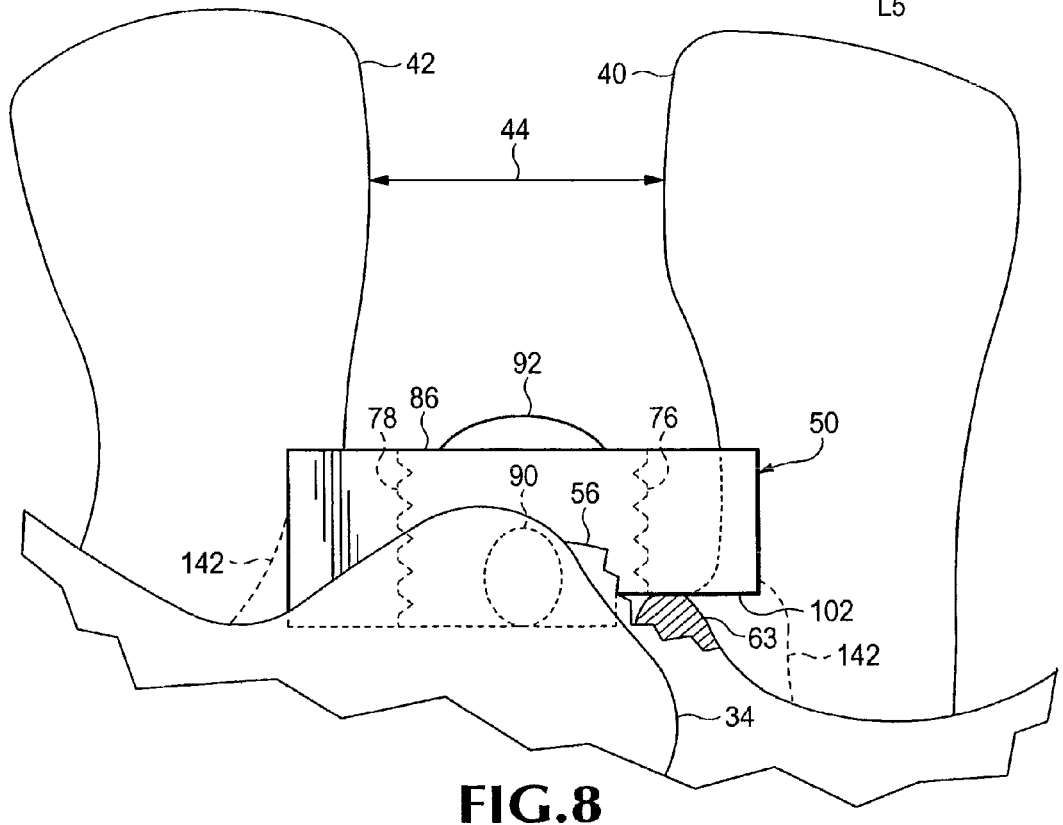
FIG. 8 is a partially broken away view similar to a portion of FIG. 2, at an enlarged scale.
Figure 11:
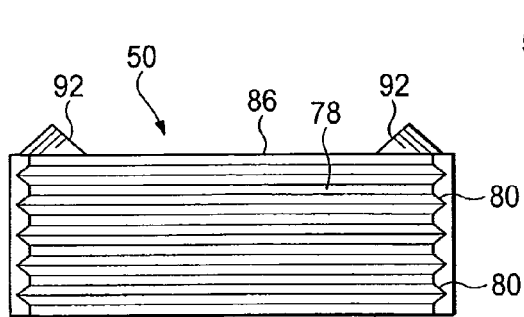
FIG. 11 is an elevational view showing the inferior bone-engaging face of the spacer body, shown in FIG. 10.
Figure 12:
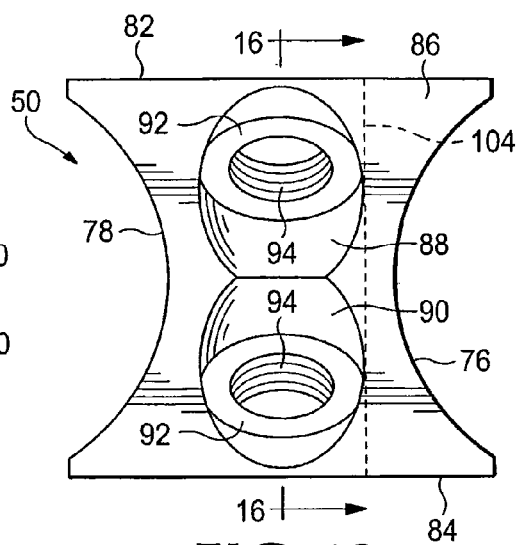
FIG. 12 is a plan view taken from the dorsal, or upper, side of the spacer body as it is shown in FIG. 10.
Figure 13:
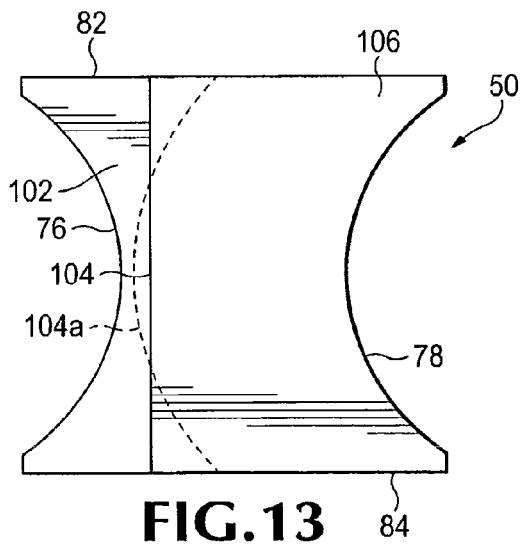
FIG. 13 is a view of the device shown in FIG. 10, taken from the ventral, or lower side as the spacer body is shown in FIG. 10.
Figure 14:
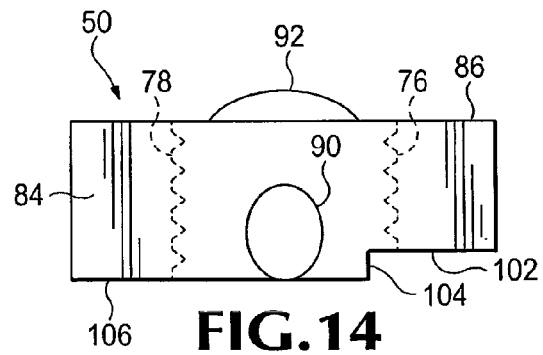
FIG. 14 is an end elevational view, showing the right lateral end face of the spacer body shown in FIG. 10.

As shown in FIGS. 13 and 14, a recessed portion including a face 102 is defined by a ledge face 104 that extends transversely across the ventral face 106 of the spacer body 50 so that the recessed face 102 can rest upon the prepared dorsal surface of the lamina 63 of the cranial (L4) vertebra as shown in FIGS. 5, 6, and 8, with the end faces 82 and 84 of the spacer body 50 snugly located between the inferior articulating processes 56 and 68. The portion defining the ventral face 106 protrudes in a downward direction as seen in FIG. 10, or a ventral direction in use, to allow the body 50 to extend into the space 62 between the vertebrae L4 and L5. As shown in broken line in FIG. 13, a ledge face 104a having the shape of a partial cylinder might be provided instead of the planar ledge face 104 shown in solid line. Such a ledge face 104a would fit more closely against the surface of the lamina 63 of the cranial (L5) vertebra when the spacer body 50 is in place between the L5 and L4 vertebrae as shown in FIGS. 5-8.

Figure 15:
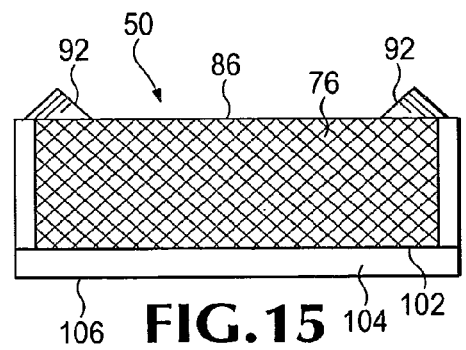
FIG. 15 is an elevational view of the superior vertebra-engaging face of the spacer body, showing an alternative non-slip textured surface configuration for the face.

As shown in FIG. 15, the surface of the cranial bone engagement face 76 may have alternatively a non-slip surface shape such as a checkered, or knurled surface including intersecting patterns of parallel grooves and ridges, and the ledge face 104 may also have such a surface texture, or may simply be smooth.

The spacer body 50 should be of a biologically implantable material. Thus it may be fashioned of cortical bone machined to the desired shape, or may be made of a machineable or castable plastics material such as polyether ether ketone (PEEK) or titanium. Similarly, the fastener locking devices 92 must be of a biologically implantable material, preferably a substantially biologically inert metal such as titanium. Also, the fasteners such as screws 52 should be of such a biologically implantable metal such as titanium or another metal unlikely to react with body fluids or interfere with use of diagnostic equipment such as magnetic resonance imagers.

Although various types of fasteners might be used, a screw 52 as shown in FIG. 7, including a coarse-threaded distal portion 108 and a relatively fine threaded proximal portion 110, advantageously engages the inferior articulating process 68 or 56 of the more cranial vertebra (L4 vertebra), and also tends to pull toward it the superior articulating process 74 or 34 of the more caudal vertebra (L5) when the screw 52 is tightened.

Once the screws 52 have been installed in the spacer body so as to extend through the facet joints on both sides, the facet joints are preferably exposed surgically and the bones of the articulating processes 34, 56, 68 and 74 may be decorticated to a depth of about one millimeter to promote growth of new bone to effect fusion. Additionally, a groove 140 may be fashioned by grinding away a small amount of the cartilaginous endplates to provide a place for insertion of a fusion-promoting material such as a local bone autograft, allograft bone, or bone extenders such as demineralized bone matrix material or bone morphogenic protein to encourage growth of new bone interconnecting the now-immobilized facet joints. Similar material 142 may be placed on and around the spacer body 50 and packed between the spacer body 50 and the decorticated spinous process and lamina surfaces of the vertebrae to be fused together, forming a matrix for regeneration of bone to fuse together the vertebrae in the position established by the spacer body 50 and the screws 52 in the facet joints. The spinous processes 40 and 42 are held separated from each other at the appropriate distance 44 by the presence of the spacer body 50, which is held in place by the screws 52 that immobilize the facet joints.

As shown in FIGS. 6 and 8, such fusion-promoting material 142 can be utilized to fill voids between the spacer body 50 and the vertebrae being fused. After installation of said fusion-promoting material, the soft tissues that had been retracted are replaced around the vertebrae being fused, so that they can provide mechanical support for the fusion-promoting gel or putty-like bone matrix and provide a supply of blood, to the extent it is not provided by the remaining cancellous bone structure, as the bones heal and fuse themselves together. The wound is then closed in the same manner as for previously utilized procedures.

Because it is unnecessary to fully expose the lateral aspect of either of the facet joints 54 and 72, the size of the opening required for the procedure described herein is significantly less than that required for installation of rods supported by pedicle screws or for installation of screws into the facet joints from a lateral aspect of such a joint. As a result, the amount of blood loss and pain is less than in such previously used procedures. Additionally, the procedure of installation of the spacer body 50 and screws 52 is less complicated, and the procedure can therefore be performed in a significantly shorter time, thus requiring shorter general anesthesia and reducing the amount of trauma suffered by the patient.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A biologically implantable device for use in fusing together a pair of adjacent vertebrae, the device comprising:
    (a) a biologically implantable spacer body having a concave cranially-facing first vertebra-engagement surface, an oppositely located concave caudally-facing second vertebra-engagement surface, a ventral face, a dorsal face, and opposite first and second lateral end faces, at least one of said vertebra-engaging surfaces being continuously curved from said first lateral end face to said second lateral end face;
    (b) a pair of fastener receptacles, defined in said spacer body, spaced apart laterally from each other, each of the fastener receptacles extending diagonally from said dorsal face through said spacer body and through a respective one of said lateral end faces, each of the fastener receptacles being adapted to receive one of a pair of bone-engagement fasteners extending therethrough and to support said one of said fasteners further extending diagonally laterally outward from said respective one of said lateral end faces of said spacer body, the fastener receptacles being located in the spacer body so as to direct each of the fasteners through respective adjacent articulating processes of a respective facet joint of a pair of adjacent vertebrae whereby each of the fasteners can immobilize the respective facet joint when said implantable device is implanted between those adjacent vertebrae; and
    (c) a pair of fasteners each engaged in a respective one of said receptacles and extending laterally outwardly at an acute angle with respect to said dorsal face, and in a ventrally inclined direction from a respective one of said opposite lateral end faces, far enough to engage and fasten together a respective facet joint between a pair of vertebrae.

2. The implantable device of claim 1 wherein said ventral face defines an engagement ledge, said engagement ledge being adapted to fit against a dorsal surface of a lamina of a cranial one of said vertebrae after hemilaminotomy of said cranial one of said vertebrae.

3. The implantable device of claim 1 including a fastener-locking device located in at least one of said fastener receptacles in said spacer body.

4. The implantable device of claim 1 wherein said fasteners are bone screws, and wherein each said fastener receptacle includes a locking device engaging a screw head of one of said bone screws so as to retain said bone screw in a selected relationship to said spacer body.

5. The implantable device of claim 1 wherein said first vertebra-engagement surface includes a plurality of ridges oriented parallel with said dorsal surface.

6. The implantable device of claim 1 wherein at least one of said first and second vertebra-engagement surfaces has a surface configuration including projections.

7. The implantable device of claim 1 wherein said ventral face includes a recessed portion adjacent to one of said first and second vertebra-engagement surfaces.

8. The implantable device of claim 1 wherein each of said first and second vertebra-engagement surfaces extends from said ventral face to said dorsal face.

9. A biologically implantable device for use in fusing together a pair of adjacent vertebrae, the device comprising:
    (a) a biologically implantable spacer body having a concave first vertebra-engagement surface, an oppositely oriented concave second vertebra-engagement surface, a ventral face, a dorsal face, and opposite first and second lateral end faces, at least one of said vertebra-engaging surface being continuously curved from said first lateral end face to said second lateral end face;
    (b) a pair of fastener receptacles defined in said spacer body, each extending from said dorsal face through said spacer body and through a respective one of said lateral end faces, each said fastener receptacle being located and directed so as to receive one of a pair of bone-engagement fasteners extending diagonally therethrough generally laterally and ventrally from said respective one of said lateral end faces of said spacer body,
    wherein at least one of said first and second vertebra-engagement surfaces includes a plurality of ridges oriented parallel with said dorsal face, said ventral face defining an engagement ledge comprising a plurality of parallel ridges, said engagement ledge being adapted to fit against a dorsal surface of a lamina of a cranial one of said vertebrae after hemilaminotomy of said cranial one of said vertebrae.

10. The implantable device of claim 1 wherein at least one of said first and second vertebra-engagement surfaces includes a plurality of ridges oriented parallel with said dorsal face, said ventral face defining an engagement ledge comprising a plurality of parallel ridges, said engagement ledge being adapted to fit against a dorsal surface of a lamina of a cranial one of said vertebrae after hemilaminotomy of said cranial one of said vertebrae.

11. The implantable device of claim 9 further comprising a pair of fasteners each engaged in a respective one of said receptacles and extending laterally outwardly at an acute angle with respect to said dorsal face, and in a ventrally inclined direction from a respective one of said opposite lateral end faces, far enough to engage and fasten together a respective facet joint between a pair of vertebrae.

12. The implantable device of claim 9 further comprising a fastener engaged in one of said receptacles, said fastener comprising a radially-extending ridge, wherein said one of said receptacles comprises a locking device that is fixedly attached to said spacer body, said locking device comprising a spring that receives and locks around said radially-extending ridge.

13. The implantable device of claim 1 wherein said spacer body includes a recessed portion defined a ledge face that extends transversely across said ventral face and a recessed face that extends parallel to said ventral face, said ledge face being planar from said first lateral end face to said second lateral end face.

14. The implantable device of claim 1 wherein said spacer body includes a recessed portion defined a ledge face that extends transversely across said ventral face and a recessed face that extends parallel to said ventral face, said ledge face being continuously curved from said first lateral end face to said second lateral end face.

15. A biologically implantable device for use in fusing together a pair of adjacent vertebrae, the device comprising:

(a) a biologically implantable spacer body having a concave cranially-facing first vertebra-engagement surface, an oppositely located concave caudally-facing second vertebra-engagement surface, a ventral face, a dorsal face, and opposite first and second lateral end faces, at least one of said vertebra-engaging surfaces being continuously curved from said first lateral end face to said second lateral end face;

(b) a pair of fastener receptacles, defined in said spacer body, spaced apart laterally from each other, each of the fastener receptacles extending diagonally from said dorsal face through said spacer body and through a respective one of said lateral end faces, each of the fastener receptacles being adapted to receive one of a pair of bone-engagement fasteners extending therethrough and to support said one of said fasteners further extending diagonally laterally outward from said respective one of said lateral end faces of said spacer body, the fastener receptacles being located in the spacer body so as to direct each of the fasteners through respective adjacent articulating processes of a respective facet joint of a pair of adjacent vertebrae whereby each of the fasteners can immobilize the respective facet joint when said implantable device is implanted between those adjacent vertebrae; and (c) a fastener engaged in one of said receptacles, said fastener comprising a radially-extending ridge, wherein said one of said receptacles comprises a locking device that is fixedly attached to said spacer body, said locking device comprising a spring that receives and locks around said radially-extending ridge.

\* \* \* \* \*